(12) United States Patent
Hu et al.

(10) Patent No.: US 7,728,156 B2
(45) Date of Patent: Jun. 1, 2010

(54) METHOD OF PERFORMING SUGAR DEHYDRATION AND CATALYST TREATMENT

(75) Inventors: Jianli Hu, Kennewick, WA (US); Johnathan E. Holladay, Kennewick, WA (US); Xinjie Zhang, Burlington, MA (US); Yong Wang, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 251 days.

(21) Appl. No.: 11/342,146

(22) Filed: Jan. 26, 2006

(65) Prior Publication Data
US 2007/0173653 A1    Jul. 26, 2007

(51) Int. Cl.
| | |
|---|---|
| C07C 29/00 | (2006.01) |
| C07D 315/00 | (2006.01) |
| C07D 493/00 | (2006.01) |
| C07H 1/00 | (2006.01) |
| C07H 17/00 | (2006.01) |
| C07H 5/04 | (2006.01) |
| C07H 1/06 | (2006.01) |
| C13K 5/00 | (2006.01) |

(52) U.S. Cl. .................. 549/464; 549/417; 536/18.5; 536/18.6; 536/18.7; 536/55.3; 536/123.1; 536/124; 536/126; 568/902

(58) Field of Classification Search ............... 536/18.5, 536/18.6, 18.7, 55.3, 123.1, 124, 126; 549/417, 549/464; 568/902

See application file for complete search history.

(56) References Cited

U.S. PATENT DOCUMENTS

| | | | |
|---|---|---|---|
| 3,160,641 | A | 12/1964 | Hartmann et al. |
| 4,297,290 | A | 10/1981 | Stockburger |
| 4,408,061 | A | 10/1983 | Salzburg et al. |
| 4,506,086 | A | 3/1985 | Salzburg et al. |
| 4,564,692 | A | 1/1986 | Feldmann et al. |

(Continued)

FOREIGN PATENT DOCUMENTS

CA        1178288        11/1984

(Continued)

OTHER PUBLICATIONS

Fleche, et al., "Isosorbide" Starch/Starke, vol. 38, 1986, pp. 26-30.

(Continued)

*Primary Examiner*—Taylor Victor Oh
(74) *Attorney, Agent, or Firm*—Wells St. John P.S.

(57) ABSTRACT

The invention includes a method of treating a solid acid catalyst. After exposing the catalyst to a mixture containing a sugar alcohol, the catalyst is washed with an organic solvent and is then exposed to a second reaction mixture. The invention includes a process for production of anhydrosugar alcohol. A solid acid catalyst is provided to convert sugar alcohol in a first sample to an anhydrosugar alcohol. The catalyst is then washed with an organic solvent and is subsequently utilized to expose a second sample. The invention includes a method for selective production of an anhydrosugar. A solid acid catalyst is provided within a reactor and anhydrosugar alcohol is formed by flowing a starting sugar alcohol into the reactor. The acid catalyst is then exposed to an organic solvent which allows a greater amount of additional anhydrosugar to be produced than would occur without exposing the acid catalyst to the organic solvent.

14 Claims, 9 Drawing Sheets

U.S. PATENT DOCUMENTS

| | | | |
|---|---|---|---|
| 4,861,513 A | 8/1989 | Lueders et al. | |
| 5,093,535 A | 3/1992 | Harrison et al. | |
| 6,013,812 A | 1/2000 | Haas et al. | |
| 6,124,443 A | 9/2000 | Darsow | |
| 6,392,062 B1 | 5/2002 | Haas | |
| 6,407,266 B2 | 6/2002 | Bhatia | |
| 6,639,067 B1 | 10/2003 | Brinegar et al. | |
| 6,689,892 B2 | 2/2004 | Andrews et al. | |
| 6,693,209 B2 | 2/2004 | Van Es et al. | |
| 7,439,352 B2 | 10/2008 | Moore et al. | |
| 2002/0052516 A1 | 5/2002 | Moore et al. | |
| 2003/0097028 A1 | 5/2003 | Fuertes | |
| 2003/0229235 A1 | 12/2003 | Bhatia | |
| 2004/0030161 A1 | 2/2004 | Bhatia | |
| 2004/0110969 A1 | 6/2004 | Fleche et al. | |
| 2004/0110994 A1 | 6/2004 | Bhatia | |

FOREIGN PATENT DOCUMENTS

| | | |
|---|---|---|
| EP | 0061055 A1 | 9/1982 |
| EP | 0201067 A2 | 11/1986 |
| EP | 0380402 A1 | 8/1990 |
| EP | 0915091 A2 | 5/1999 |
| EP | 1179535 A1 | 2/2002 |
| EP | 1179536 A1 | 2/2002 |
| WO | 9721697 A1 | 6/1997 |
| WO | 0014081 A1 | 3/2000 |
| WO | 0041985 | 7/2000 |
| WO | 0172136 A1 | 10/2001 |
| WO | 0194352 A1 | 12/2001 |
| WO | 0239957 A2 | 5/2002 |
| WO | 03022064 A1 | 3/2003 |
| WO | 03089436 A1 | 10/2003 |
| WO | 03089445 A1 | 10/2003 |
| WO | 2005047228 A1 | 5/2005 |

OTHER PUBLICATIONS

2006 Chemical Abstracts Catalog, published 2006 by Chemical Abstracts Service, p. 52.

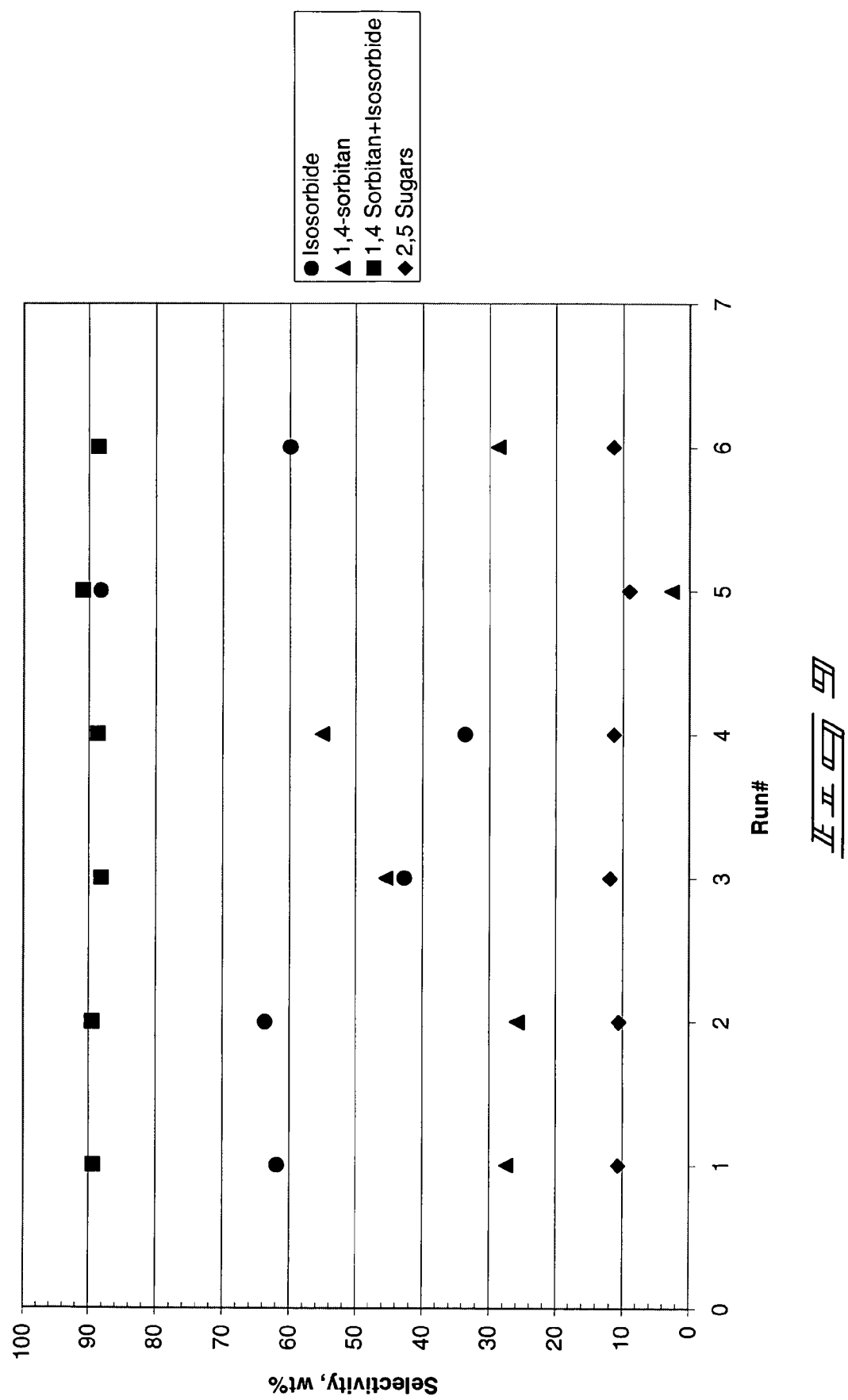

METHOD OF PERFORMING SUGAR DEHYDRATION AND CATALYST TREATMENT

CONTRACTUAL ORIGIN OF THE INVENTION

This invention was made with Government support under contract DE-AC0676RLO-1830, awarded by the U.S. Department of Energy. The Government has certain rights in this invention.

TECHNICAL FIELD

The invention pertains to methods for producing anhydrosugar alcohols, methods for selective production of anhydrosugars from a sugar alcohol, and methods of treating a catalyst.

BACKGROUND OF THE INVENTION

Anhydrosugar, dianhydrosugars (also known as sugar alcohols) and their derivatives are commercially valuable for a variety of applications including therapeutic uses and use as copolymers to improve properties of polymer materials. Conventional dehydration of sugars to produce anhydrosugars and/or dianhydrosugar alcohols, typically utilizes batch processing with a mineral acid catalyst. However, such conventional production of dianhydrosugars and/or anhydrosugars can be expensive and inefficient. Additionally, conventional processes can be environmentally unfriendly.

It is desirable to develop alternative methods for producing anhydro- and dianhydrosugar alcohols.

SUMMARY OF THE INVENTION

In one aspect, the invention encompasses a method of treating a catalyst. A solid acid catalyst is exposed to a first reaction mixture which contains at least one sugar alcohol. After this exposing, the catalyst is washed with an organic solvent and is then exposed to a second reaction mixture.

In one aspect, the invention encompasses a process for production of anhydrosugar alcohol. A solid acid catalyst is provided, and a first sample containing a sugar alcohol is exposed to the solid acid catalyst. At least some of the sugar alcohol in the first sample is converted to an anhydrosugar alcohol in the presence of the catalyst. The solid acid catalyst is then washed with an organic solvent and is subsequently utilized to expose a second sample containing a sugar alcohol to convert an amount of the sugar alcohol in the second sample to an anhydrosugar alcohol.

In one aspect, the invention encompasses a method for selective production of an anhydrosugar product. A solid acid catalyst is provided within a reactor and a first quantity of an anhydrosugar alcohol is formed by flowing an initial amount of the solution containing a starting sugar alcohol into the reactor. The acid catalyst is subsequently exposed to an organic solvent and, after such exposing, is utilized to form a second quantity of the anhydrosugar alcohol by flowing an additional amount of solution comprising the starting sugar alcohol into the reactor. The amount of starting sugar alcohol converted to the anhydrosugar alcohol is greater than would be produced in an absence of exposing the acid catalyst to the organic solvent.

BRIEF DESCRIPTION OF THE DRAWINGS

FIG. 9 shows product selectivity for sorbitol dehydration under continuous reactor conditions in accordance with the invention.

DETAILED DESCRIPTION OF THE PREFERRED EMBODIMENTS

Figure 1:
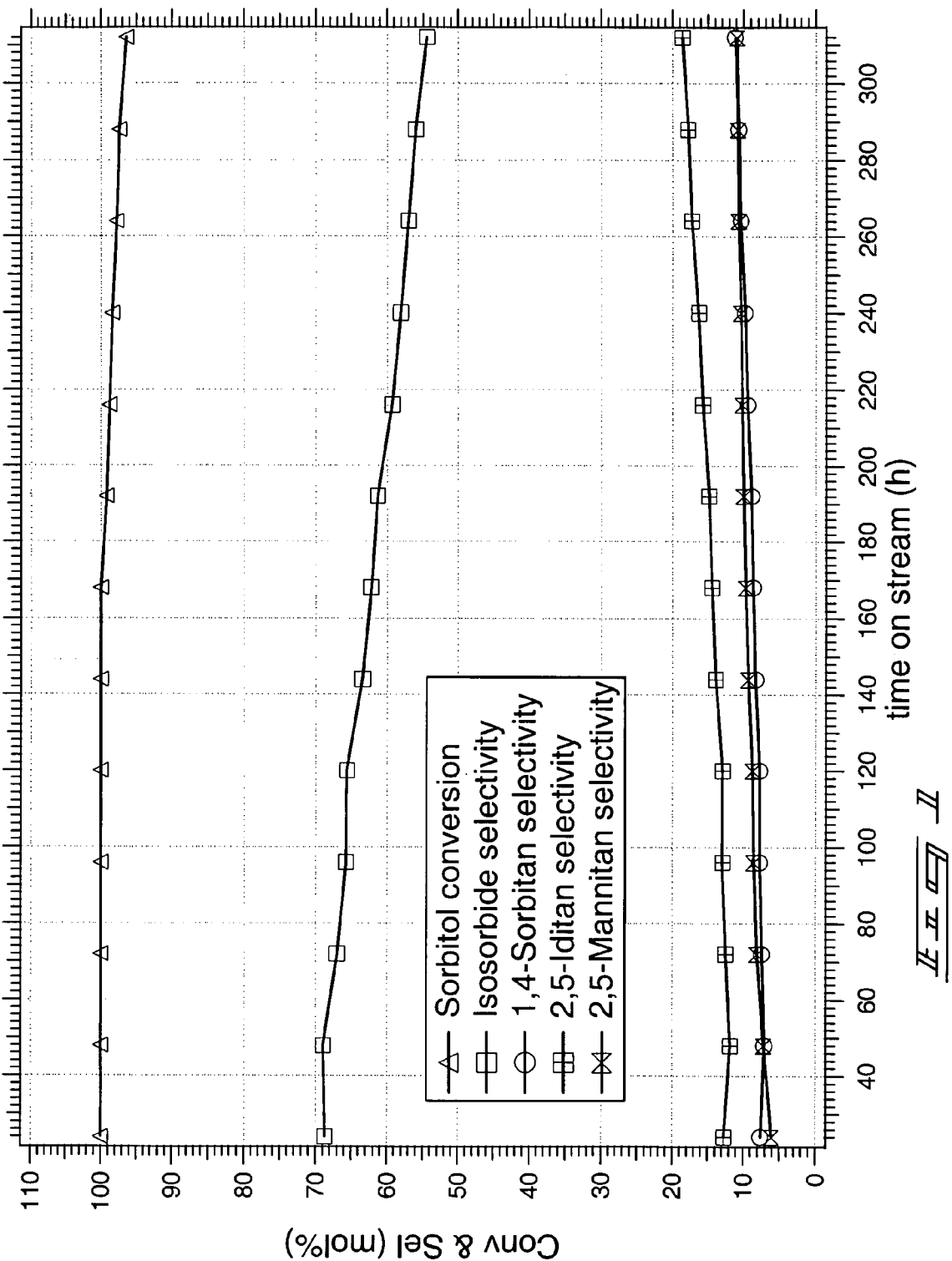
FIG. 1 shows the efficiency and selectivity of product production utilizing a solid acid catalyst in the absence of treatment in accordance with the invention.

Preferred embodiments of the invention are described below with reference to the following accompanying drawings. This disclosure of the invention is submitted in furtherance of the constitutional purposes of the U.S. Patent Laws "to promote the progress of science and useful arts" (Article 1, Section 8).

In general, the invention provides a process for production of anhydrosugar alcohols. The process generally includes exposing a sugar alcohol to a solid acid catalyst to convert at least some of the sugar alcohol to an anhydrosugar alcohol. The process includes washing of the solid acid catalyst to assist in retaining and/or enhancing catalyst activity, and to lengthen catalyst life.

More specifically, the invention pertains to dehydration reactions involving dehydration of sugar alcohols and/or further dehydration of anhydrosugars. The invention is not limited to any particular sugar alcohol or anhydrosugar starting material, and can be utilized for dehydration of a single sugar alcohol, a single anhydrosugar, and mixtures containing one or more sugar alcohol and/or anhydrosugars. The invention can be particularly useful for dehydration of sorbitol for production of sorbitan and/or isosorbide, or for further dehydration of the anhydrosugar 1,4-sorbitan to isosorbide. Other sugar alcohols and anhydrosugars of particular interest for utilizing as starting sugar alcohols for dehydration in accordance with the invention, include but are not limited to, mannitol, xylitol, arabinitol, sorbitol and mixtures thereof.

Dehydration reactions in accordance with the invention can typically utilize one or more solid acid catalysts for catalyzing the dehydration. Conventional use of solid acid catalysts for performing dehydration reactions have shown to be problematic due to catalysts fouling and/or deactivation. In particular, catalysts such as resin acid catalysts are quickly deactivated, resulting in slower rate of conversion and increased production of less desirable products. Such deactivation can be attributed to one or more of catalyst proton replacement by metal ions, catalyst desulfonization, adsorption of sugar, oligomer and/or polymer material onto the catalyst, and resin breakdown or cross-linking. Acid catalyst resin deactivation which can occur in sorbitol dehydration reactions can result in slower conversion of sorbitol and higher production of 2,5-sugars (2,5-iditan and 2,5-mannitan) resulting in decreased selectivity toward 1,4-sorbitan, 3,6-sorbitan, and conversion of such desirable intermediates to the dianhydrosugar isosorbide. Accordingly, conventional use of solid acid catalysts has been limited to batch production of anhydrosugars.

The dehydration methods and catalyst treatment methods of the invention can allow continuous operation for dehydration production of anhydrosugars. It is to be understood, however, that the reaction methodology and catalyst treatment can also be utilized in conjunction with batch wise processes. Processing in accordance with the invention typically involves providing a starting material comprising one or more sugar alcohols, mono anhydrosugars, or mixtures thereof. The starting material can comprise one or more sugar alcohols in an absence of solvent, or as a mixture or a solution. Where a solvent is provided, the resulting mixture can preferably contain from about 30% to 100% sugar alcohol/anhydrosugar. An exemplary starting mixture can comprise, for example a solution containing 70% sugar alcohol in water.

The starting material can be exposed to a solid acid catalyst in accordance with the invention by providing the solid acid catalyst within a reactor, and introducing the starting material into the reactor. The reactor can be a batch reactor or can more preferably be a continuous reactor, such as for example a quartz fixed-bed or other fixed-bed reactor. Where a continuous process is utilized, exposing the starting material to the catalyst can comprise, for example flowing the starting material through the reactor containing the solid acid catalyst.

Numerous solid acid catalysts are available for utilization in accordance with methodology of the invention. The solid acid catalysts can comprise one or more solid acid materials. The solid acid catalyst can be used independently or alternatively can be utilized in combination with one or more mineral acid or other types of catalysts. Exemplary solid acid catalysts which can be utilized include but are not limited to, heteropoly acids, acid resin type catalysts, meso-porous silicas, acid clays, sulfated zirconia, molecular sieve materials, zeolites, and acid material on a thermo-stable support. Where an acid material is provided on a thermo-stable support, the thermo-stable support can include for example, one or more of silica, tin oxide, niobia, zirconia, titania, carbon, and alpha-alumina.

Exposure of the starting material to the solid acid catalyst can result in conversion of at least some of the sugar alcohols/anhydrosugars in the initial material to anhydrosugars and/or dianhydrosugar alcohol. It is noted that for many starting materials the conversion can result in production of one or more monomeric byproducts and can also result in production of various oligomer and/or polymer materials. Polymer formation during the dehydration reaction can result in catalyst fouling. Many types of solid acid catalysts are difficult, if not impossible, to regenerate by thermo methods. However, in accordance with the invention, the solid acid catalyst utilized for exposure and conversion of an initial material is treated to remove at least some of any polymer and/or other fouling material present after the exposure.

Treatment of the catalyst, in accordance with the invention, can typically comprise washing the acid catalyst with one or more organic solvents. The washing can comprise, for example flowing the one or more organic solvents through the reactor containing the % solid catalyst. Alternatively, and especially where batch wise production is utilized, the washing can comprise adding the one or more organic solvents to the acid catalyst and can further comprise stirring or other mixing techniques.

Numerous organic solvents are available for utilization for washing solid acid catalysts in accordance with the invention. The particular organic solvent(s) utilized can depend upon factors such as, for example, the type of acid catalyst utilized and/or the presence of and type of any supporting material. Exemplary organic solvents which can be utilized include but are not limited to: esters, such as ethyl acetate; ketones, such as methyl ethyl ketone; alcohols, such as ethanol; aromatic hydrocarbons, such as xylene; ethers such as diethyl ether; cyclic ethers, such as tetrahydrofuran (THF); halogenated hydrocarbons, such as methylene chloride, and other similar polar aprotic solvents.

After washing the catalyst, the catalyst can be used to expose a second starting material. The second starting material can be similar or identical to the first starting material, or can comprise a different material comprising differing sugar alcohols and/or solvents relative to the earlier starting material. In the presence of the solid acid catalyst, dehydration of sugar alcohols and/or anhydrosugar alcohols present in the second starting material can be dehydrated to form one or more anhydrosugar alcohol products. The described catalyst washing can allow enhanced conversion and/or selectivity of anhydrosugar production after washing relative to an amount and/or selectivity which would occur in an absence of the washing. The use of organic solvent or washing solid acid catalysts can improve catalyst longevity relative to alternative washing procedures such as, for example utilization of water or water-based wash solutions. The utilization of organic solvent washing can decrease or prevent fouling by removal and/or prevention of adsorption of sugar alcohols, oligomers and/or polymers on the catalyst.

EXAMPLES

The effectiveness and advantages of the methodology presented above was examined by comparison to alternative or conventional techniques. An initial study included a continuous isosorbide production reaction utilizing sorbitol as an initial starting material and exposure of the starting material to the solid acid catalyst AMBERLYST® 35 resin. The reaction was conducted at around 125° C. The conversion and selectivity during the reaction as a function of time is set forth in FIG. 1. As shown, in an absence of catalyst regeneration or washing, the reaction efficiency decreases over time. While sorbitol conversion decreased slightly, the yield to isosorbide was significantly decreased. The decrease in yield is apparently due to a lower rate of conversion of the 1,4-sorbitan intermediate to isosorbide. However, there was also a significant increase in production of 2,5-sugars which do not go on to form isosorbide.

Figure 2:
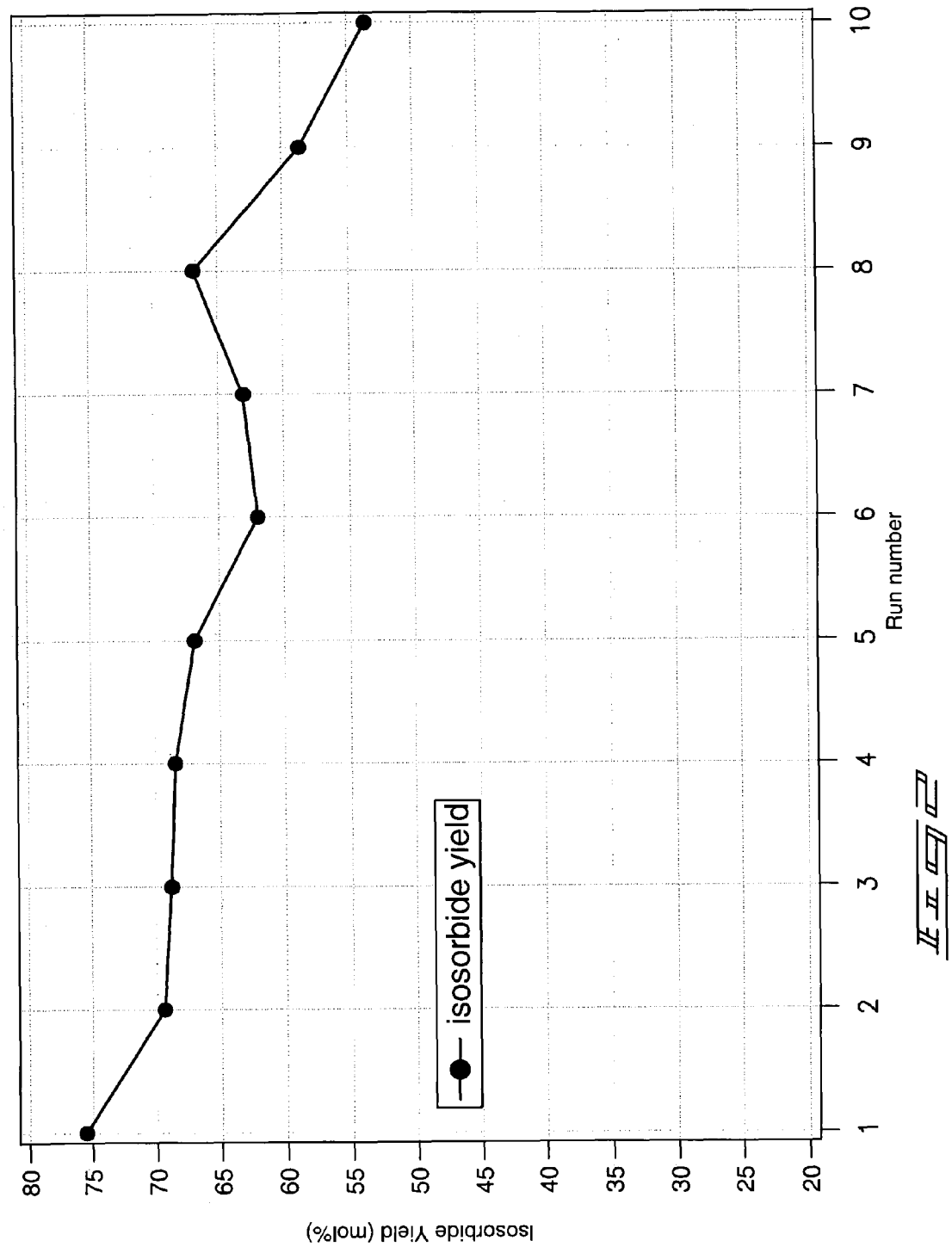
FIG. 2 shows the yield of isosorbide utilizing a solid acid catalyst over sequential batch reactions without treating the catalyst in accordance with the invention.

An additional study utilizing batch conditions was also performed. The results of such batch wise processing are set forth in FIG. 2. Ten sequential batch reactions were performed utilizing AMBERLYST® (Rohm & Haas Company Philadelphia, Pa.) 35. Over the course of the ten runs, the yield of isosorbide dropped from approximately 75.5% (run 1) to 53.6% (run 10). The 30% drop in yield reflects lower catalyst activity and efficiency.

Catalyst stability for partial conversion of sorbitol was studied utilizing AMBERLYST® 36 resin in a continuous process using a fixed-bed quartz reactor. Approximately 5 g of wet AMBERLYST® 36 (6.5 ml, 2.25 g dry resin) was utilized. The starting material was a feed of 70% sorbitol solution at a flow rate of 0.021 ml/min. The experiment was conducted over 1,000 hours at a sorbitol conversion of approximately 80% throughout the experiment. The starting reaction temperature was 123° C. with an ending reaction temperature of 127° C. The reactor residence time (liquid hourly space velocity, LHSV) was approximately 0.2 hr$^{-1}$.

Figure 3:
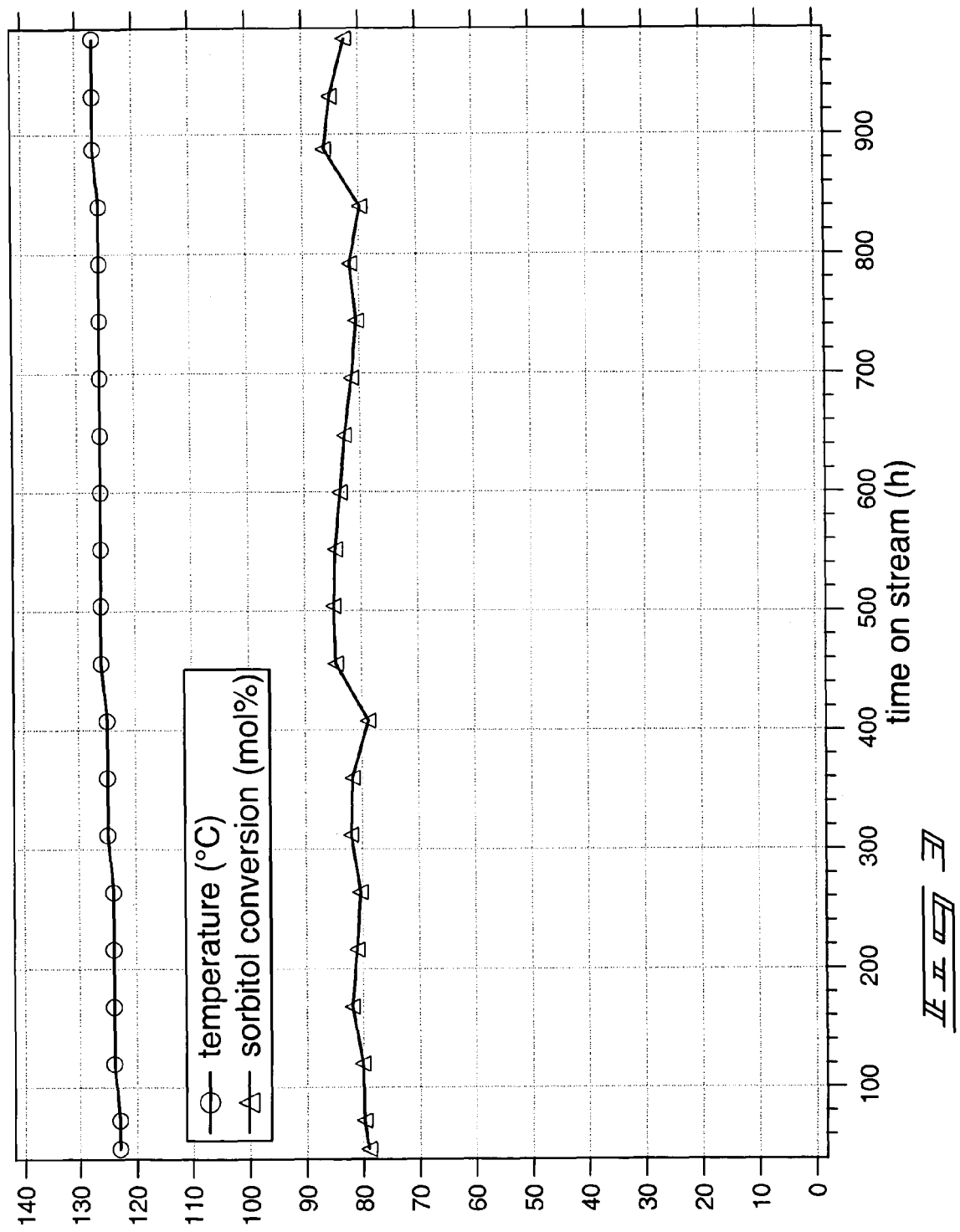
FIG. 3 depicts the results of a study of catalyst stability utilizing methodology in accordance with one aspect of the invention.

The observed catalyst stability as determined by stability of reaction temperature at approximately 80 percent sorbitol conversion over time is presented in FIG. 3. The steady conversion rate at a temperature increase of approximately 4° C. observed over 1000 hours indicates that the catalyst is stable for incomplete conversion of sorbitol. In comparison, as shown in FIG. 1, increased or complete conversion of sorbitol results in increased catalyst deactivation. Accordingly, the ability to regenerate/reactivate the catalyst utilizing methodology of the invention is increasingly advantageous for allowing increased conversion with decreased loss of activity, resulting in increased product yield and longer catalyst life for reactions at full conversion.

Figure 4:
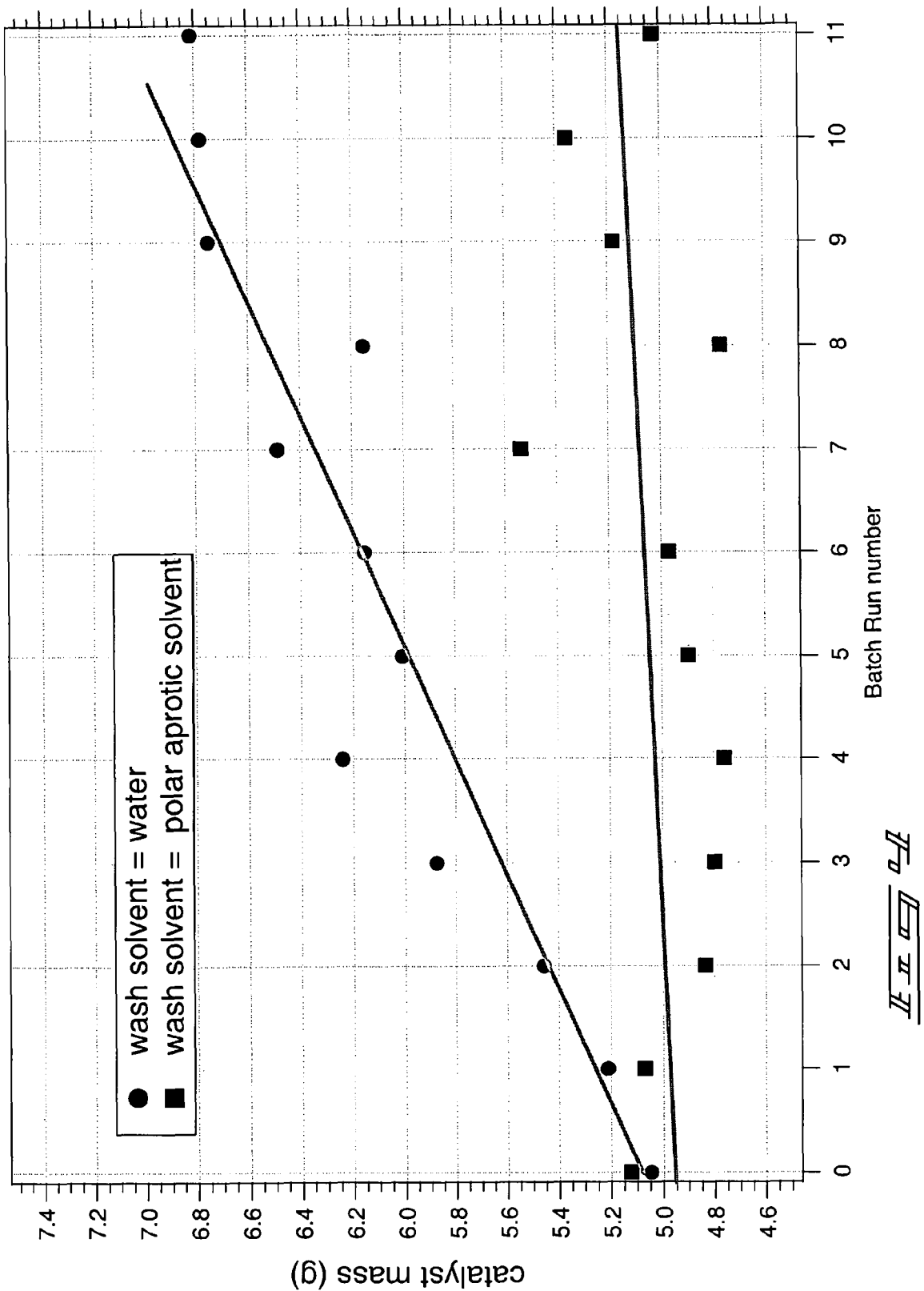
FIG. 4 shows catalyst weight over time for Experiments A and B.
Figure 5:
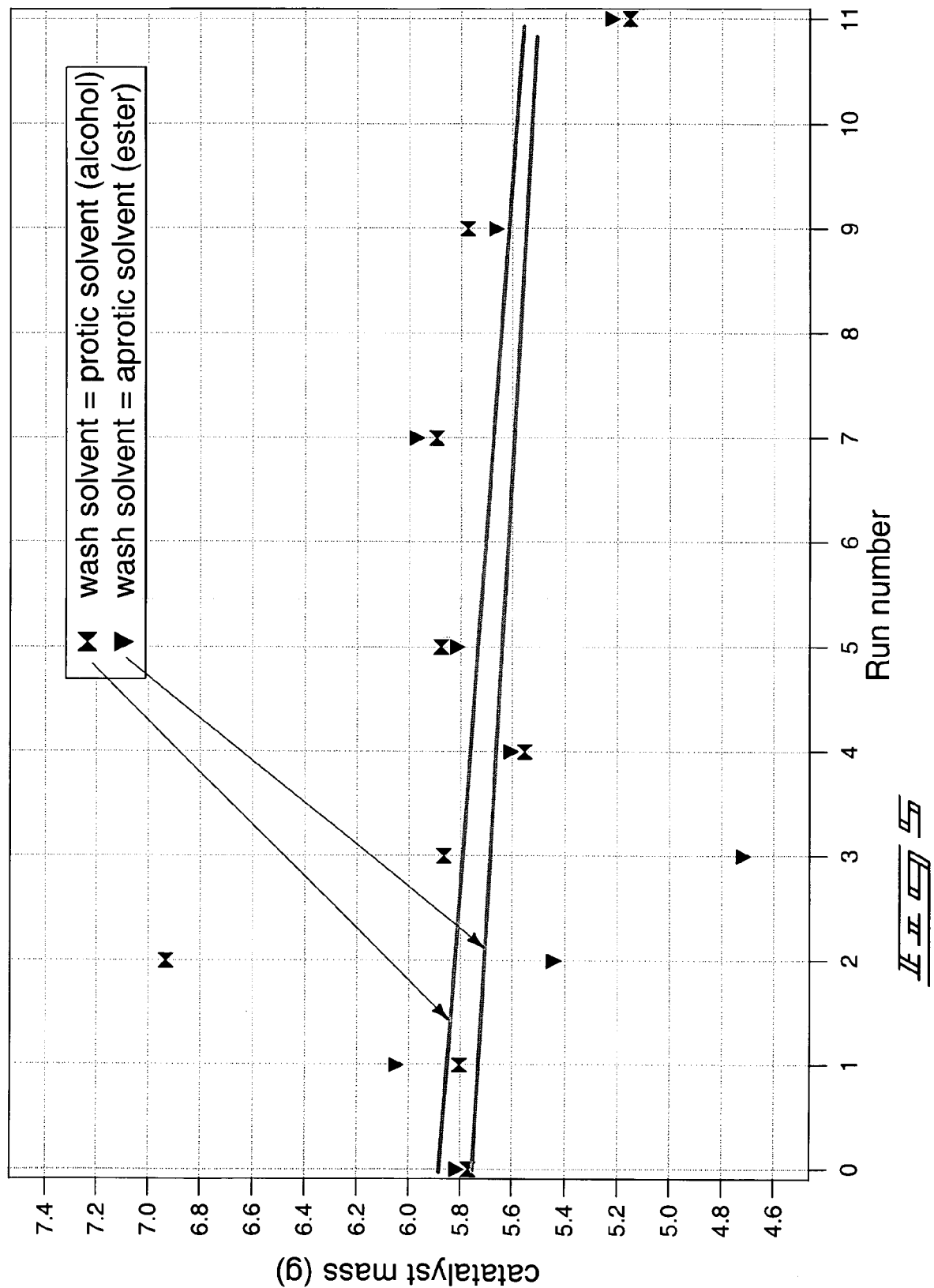
FIG. 5 shows the catalyst weight over time Experiments C and D.

The mass of the catalyst over time was also studied in the presence and absence of washing. FIG. 4 and FIG. 5 present the results of experiments indicated as experiments A through D. Each of experiments A through D consisted of eleven batch runs. Approximately 5 g of a resin catalyst (AMBERLYST® 16) was used in each experiment. Each run was two hours in length under vacuum (76 mmHg) at a temperature of 135° C. Between each run, the catalyst was washed, dried, weighed, and was then reused such that each initial 5 g of resin was utilized for the entirety of the eleven runs performed in each of the experiments. In experiment A, water was utilized as the wash solvent. The catalyst was washed with water, dried, and weighed between each of the eleven runs. In experiment B, acetone was used as the wash solvent. In experiment C, ethanol was utilized as the wash solvent, and in experiment D, ethyl acetate was utilized as the wash solvent.

The results of experiments A and B are presented in FIG. 4. The results of experiments C and D are presented in FIG. 5. The drying protocol utilized for experiments A and B were slightly different than those utilized for Experiments C and D. For experiments A and B, the catalyst was dried over night at 110° C. after washing. In experiments C and D, the catalyst was dried for two hours at 110° C. after washing. The weight of the catalyst after drying in Experiment A showed a steady increase from Run 1 through Run 10. However, when an organic solvent was used to wash the catalyst (experiments B through D), the catalyst mass did not increase appreciatively over the eleven runs.

Figure 6:
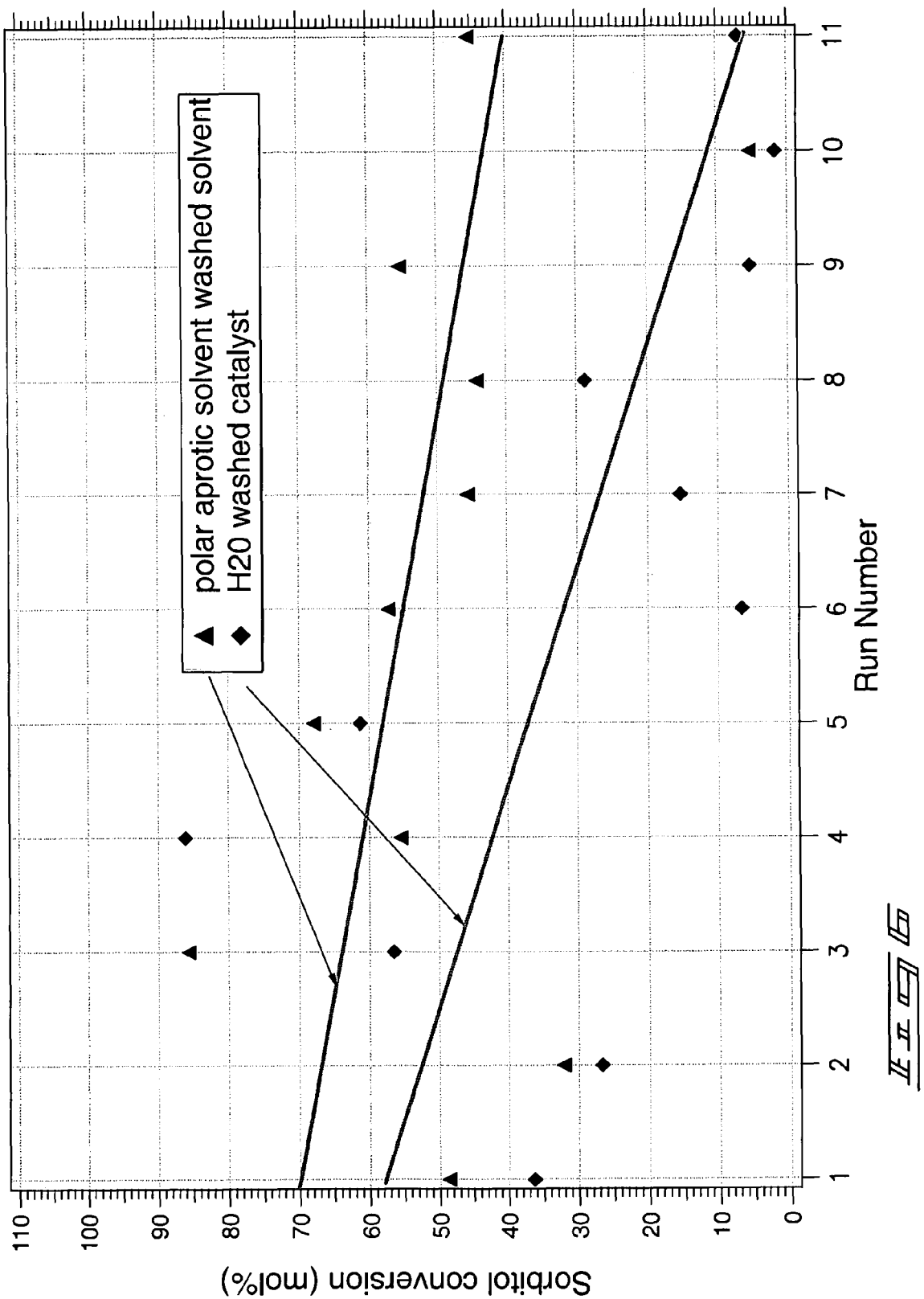
FIG. 6 shows sorbitol conversion experiment results A and B, where water was utilized to wash catalyst in Experiment A, and where acetone was utilized for catalyst washing in Experiment B.
Figure 7:
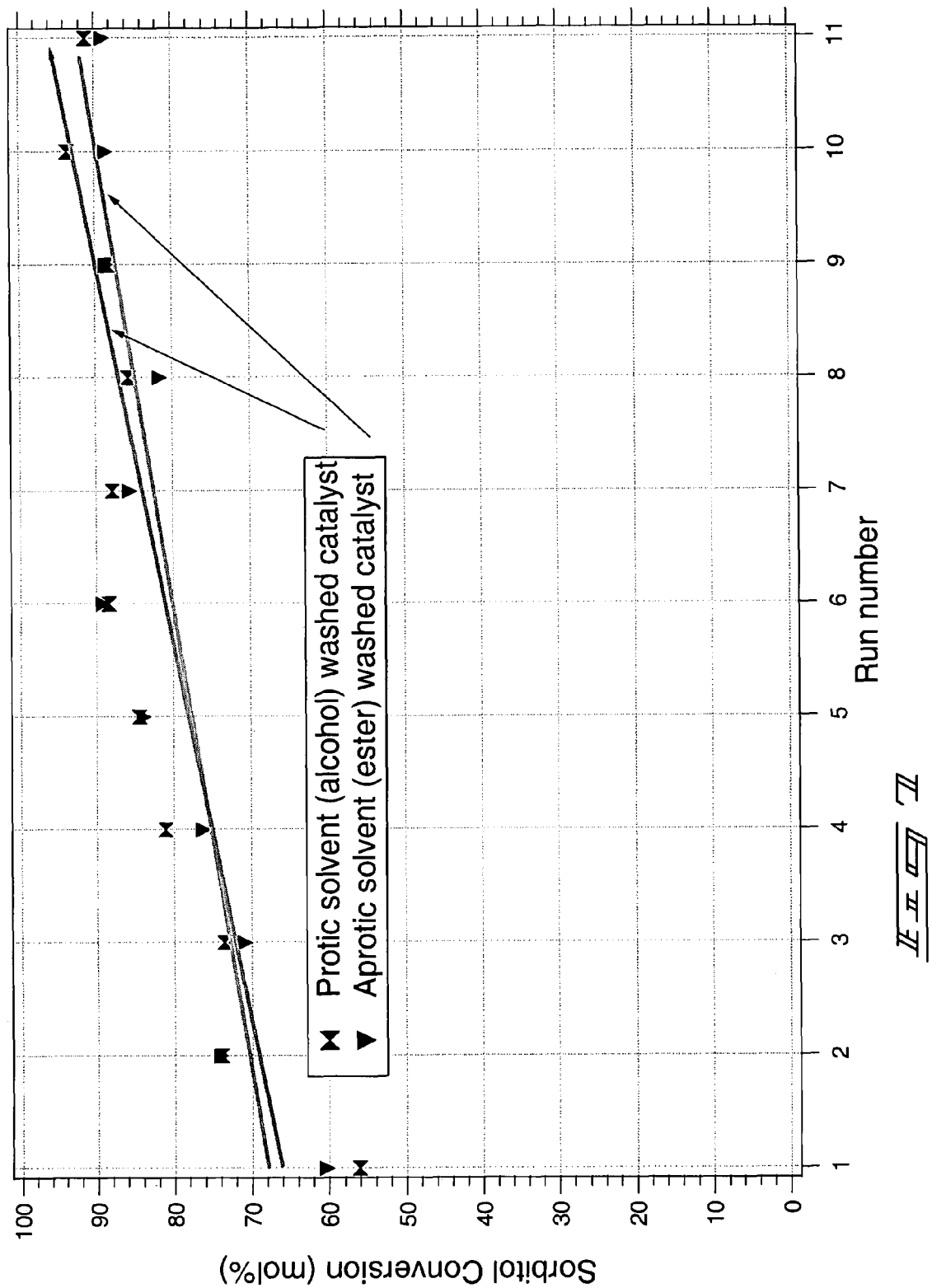
FIG. 7 shows results of Experiment C which utilized ethanol for washing of the solid acid catalyst, and Experiment D which utilized ethyl acetate for washing the solid acid catalyst.

FIGS. 6 and 7 show the sorbitol conversions observed in experiments A through D. In experiment A where water was utilized to wash the catalyst there was significant loss of catalyst activity. In experiment B there was a modulation of activity initially, with fairly stable activity over the last six runs. Catalyst activity was actually observed to improve in experiments C and D utilizing ethanol or ethyl acetate respectively as washed solvents.

Based on the results above, the estimated resin catalyst life utilizing the reaction process and treatments in accordance with the invention is approximately 5,000 hours. Similar increased lifetime is expected for other solid acid catalysts. Accordingly, the methodology of the invention can be utilized to increase cost effective production of anhydrosugars relative to conventional methodology.

Additional studies were conducted utilizing a vacuum continuous flow reactor. AMBERLYST® 36 was used as a representative solid acid catalyst to study the effectiveness and advantages of performing methodology of the invention under continuous flow reactor conditions. For the continuous operation study, 2 grams of AMBERLYST® 36 was mixed with about 10 grams of 2 mm glass beads, and was packed into the reactor. Glass beads were utilized to minimize reactor plugging due to the small size of AMBERLYST® 36 resin. The reaction feedstock contained 70% sorbitol in water. The continuous reaction conditions involved a series of rounds; where for each round feedstock was flowed into the reactor for 4 hours followed by 1 hour of ketone-comprising solvent wash at 70° C. The LHSV was 1.0H$^{-1}$.

Figure 8:
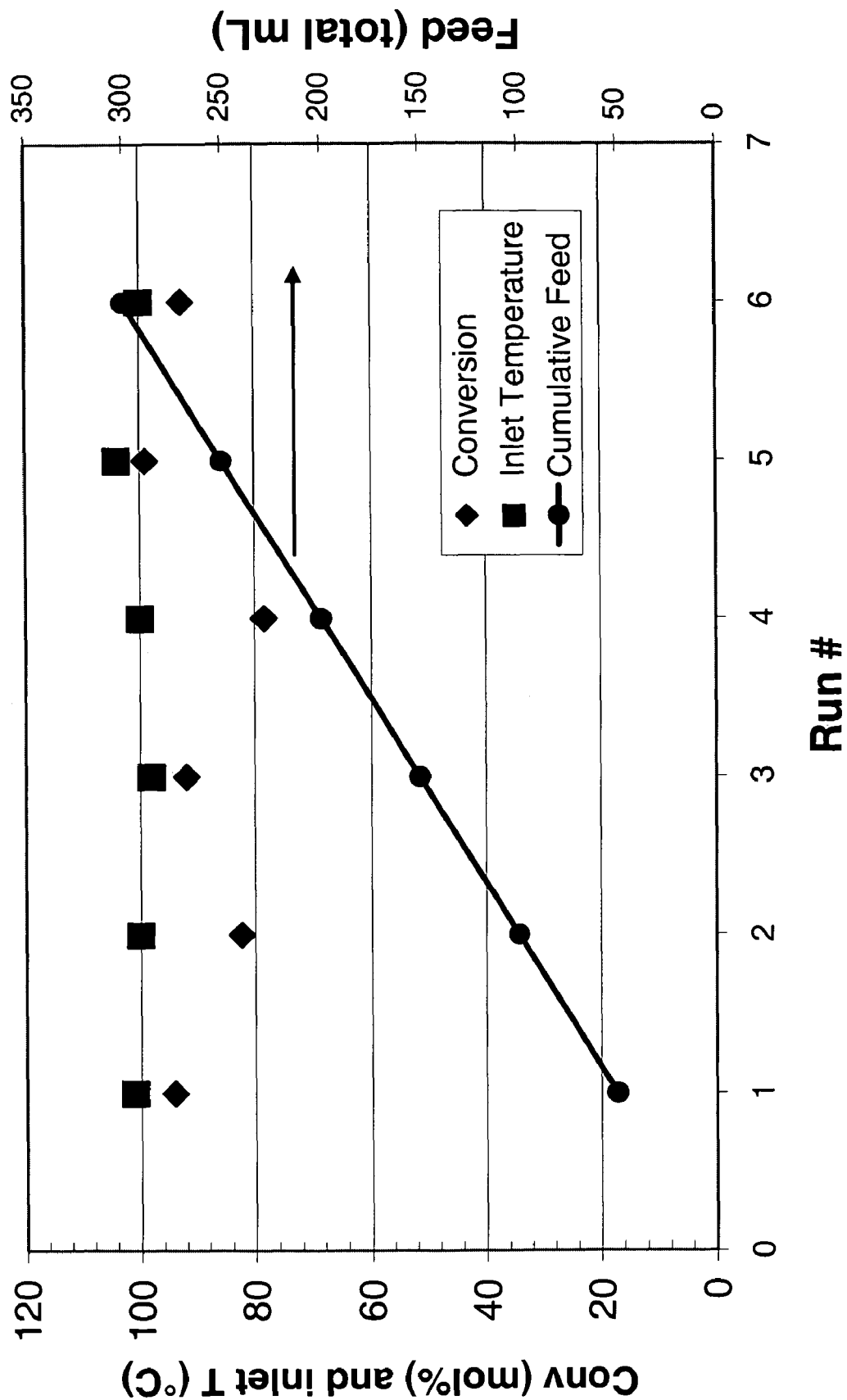
FIG. 8 shows the conversion of sorbitol and effects of temperature non-uniformity for a continuous process reactor with washing of the solid acid catalyst in accordance with methodology of the invention.

The results of 7 rounds of dehydration in the continuous process are provided in FIGS. 8 and 9. Due to vigorous evaporation of water during the dehydration reaction, the temperature of the catalyst bed was not uniform. The temperature control point was set at the reactor inlet with the inlet temperature for the reactions being 100° C. The reaction pressure was 8 mmHg. Fluctuation of sorbitol conversion (shown in FIG. 8) was strongly associated with the average operating temperature along the length of the catalyst bed. The overall trend of conversion indicated that catalyst activity was retained throughout the 7 rounds during which 300 ml of feed material was processed. It may be advantageous to use a higher sugar alcohol concentration, up to 100%, as the feedstock to enhance temperature uniformity throughout the catalyst bed.

The product selectivity for 2,5-sugars, 1,4-sorbitan and isosorbide during the continuous process is presented in FIG. 9. As shown, selectivity to 2,5-sugars remained constant (approximately 10%) throughout each of the 7 rounds whereas changes in selectivity to 1,4-sorbitan and isosorbide were observed. This result implies that the formation of 2,5-sugars reached equilibrium under the operating conditions utilized and that selectivity to desired products is sensitive to uniformity of catalyst bed temperature.

The results of the studies in the continuous reactor indicate that catalyst life can be extended by washing the catalyst with an appropriate solvent in accordance with methodology of the invention. Wash intervals are not limited to the particular intervals utilized in the example reaction and can be adjusted as appropriate. Studies of the invention indicate that for continuous processes, extended time on line without catalyst washing can result in irreversible loss of activity or even irreversible inactivation of the catalyst. Therefore, the intervals between washing events are preferably sufficiently short to provide washing of the catalyst prior to significant or irreversible deactivation of the catalyst. A preferable wash interval to maintain regeneration ability of the catalyst can be less than or equal to every 100 hours online. In some instances, a wash interval of about 24 hours online is more preferable and, under particular conditions, a wash interval of about every 4 hours is even more preferred. It is to be understood that the invention contemplates non-equivalent time intervals between catalyst washes, such as where catalytic activity is monitored during the continuous reaction.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A process for production of an anhydrosugar alcohol comprising:

provide a solid acid catalyst comprising at least one member selected from the group consisting of an acid resin catalyst, a heteropoly acid, meso-porous silicas, acid clays, sulfated zirconia, molecular sieves, and;

exposing a first starting material consisting of a sugar alcohol and optionally water to the solid acid catalyst;

in the presence of the solid acid catalyst, converting at least some of the sugar alcohol in the first starting material to an anhydrosugar alcohol and forming a polymeric byproduct material;

washing the solid acid catalyst with an organic solvent to remove polymeric byproduct material from the solid acid catalyst;

after the washing, exposing a second starting material comprising a sugar alcohol to the solid acid catalyst; and in the presence of the solid acid catalyst, converting an amount of the sugar alcohol in the second starting material to an anhydrosugar alcohol.

2. The method of claim 1 wherein the amount of sugar alcohol in the second starting material converted to the anhydrosugar is enhanced relative to an amount produced in an absence of the washing.

3. The method of claim 1 wherein the amount of sugar alcohol in the second starting material converted to the anhydrosugar is improved relative to an amount produced in an identical process except having the organic solvent replaced with water.

4. The method of claim 1 wherein the organic solvent comprises a polar aprotic solvent.

5. The method of claim 1 wherein the organic solvent comprises at least one member selected from the group consisting of ethyl acetate, methyl ethyl ketone, and ethanol.

6. The method of claim 1 wherein thermo-stable support is selected from the group consisting of silica, tin oxide, niobia, zirconia, titania, carbon and mixtures thereof.

7. A method for selective of production of an anhydrosugar product from a sugar alcohol, the method comprising;

providing a solid acid catalyst in a reactor, the solid acid catalyst comprising at least one member selected from the group consisting of, a heteropoly acid, meso-porous silicas, acid clays, and sulfated zirconia;

forming a first quantity of an anhydrosugar alcohol by flowing an initial amount of a solution consisting of a starting sugar alcohol and optionally water into the reactor and converting at least some of the starting sugar alcohol to the anhydrosugar alcohol within the reactor exposing the acid catalyst to an organic solvent, the exposing removing polymeric material from on the acid catalyst, the polymeric material being formed during the flowing the initial amount of solution comprising the starting sugar alcohol into the reactor; and after the exposing, forming a second quantity of the anhydrosugar alcohol by flowing an additional amount of the solution comprising the starting sugar alcohol into the reactor and converting at least some of the starting sugar alcohol in the additional amount of solution to the anhydrosugar alcohol, the second quantity being greater than would be produced in the absence of the exposing.

8. The method of claim 7 wherein the reactor is configured for continuous processing.

9. The method of claim 8 wherein the exposing the acid catalyst to an organic solvent is repeated at intervals of less than or equal to 100 hours of reaction time.

10. The method of claim 7 wherein the reactor is a batch reactor.

11. The method of claim 7 wherein the starting sugar alcohol is sorbitol and the anhydrosugar alcohol is isosorbide.

12. A method of treating a catalyst comprising:

providing a solid acid catalyst comprising at least one member selected from the group consisting of an acid resin catalyst, a heteropoly acid, meso-porous silicas, acid clays, sulfated zirconia, molecular sieves, and;

exposing the catalyst to a first reaction mixture, the reaction mixture consisting of at least one sugar alcohol and optionally water;

after the exposing, washing the solid acid catalyst with an organic solvent to remove polymeric material from on the catalyst, the organic solvent being selected from the group consisting of esters, methyl ethyl ketone, aromatic hydrocarbons, ethers, cyclic ethers, and halogenated hydrocarbons, the polymeric material being formed during the exposing to the first reaction mixture; and after the washing, exposing the catalyst to a second reaction mixture.

13. The method of claim 12 wherein the thermo-stable support is selected from the group consisting of silica, tin oxide, niobia, zirconia, titania, carbon and mixtures thereof.

14. The method of claim 12 wherein the second reaction mixture comprises at least one sugar alcohol.

* * * * *

UNITED STATES PATENT AND TRADEMARK OFFICE
CERTIFICATE OF CORRECTION

PATENT NO. : 7,728,156 B2
APPLICATION NO. : 11/342146
DATED : June 1, 2010
INVENTOR(S) : Hu et al.

It is certified that error appears in the above-identified patent and that said Letters Patent is hereby corrected as shown below:

Column 3, Line 66 – Replace "the % solid" with --the solid--.

Signed and Sealed this

Seventeenth Day of August, 2010

David J. Kappos
*Director of the United States Patent and Trademark Office*